United States Patent [19]

Nathanielsz

[11] Patent Number: 4,967,761

[45] Date of Patent: Nov. 6, 1990

[54] METHOD OF MONITORING LABOR

[75] Inventor: Peter W. Nathanielsz, Ithaca, N.Y.

[73] Assignee: Cornell Research Foundation, Inc., Ithaca, N.Y.

[21] Appl. No.: 221,691

[22] Filed: Jul. 20, 1988

[51] Int. Cl.$^5$ .............................................. A61B 5/04
[52] U.S. Cl. .................................... 128/733; 128/775
[58] Field of Search ............... 128/733, 775, 778, 782

[56] References Cited

PUBLICATIONS

Hsu et al, "Power Spectrum Analysis of Myometrial Electromyogram and Intrauterine Pressure Changes in the Pregnant Rhesus Monkey in late gestation" Am. J. Obstet. Gynecol., Aug. 1989, pp. 467–473.
Nathaniels et al, "Update on the Molecular Events of Myometrial activity during pregnancy" Perinatology Press, 1984, pp. 92–102.
Basano et al., Real–Time FFT to Monitor Muscle Fatigue, IEEE Transactions on Biomedical Eng., vol. BME-33, No. 11, Nov. 1986, pp. 1049–1051.
Phillips, Chandler A., On-line Digital Processing of Uterine Contraction Waveforms, Proceedings of the IEEE 1977 National Aerospace and Elec. Conf. Dayton Ohio, (May 17–19, 1977, p. 243.
Ducsay et al, Am. J. Obstet. Gynecol., 145:389—(1983).
Jansen et al, Am. J. Obstet. Gynecol., 134:776-783 (1979).
Nathanielsz et al, Am. J. Obstet. Gynecol., 138:653 (1980).
Krishnamurti et al, J. Reprod. Fert., 64:59 (1982).
Harbert, Am. J. Obstet. Gynecol., 129:401-408 (1977).

Primary Examiner—Max Hindenburg
Assistant Examiner—S. Getzow
Attorney, Agent, or Firm—Jones, Tullar & Cooper

[57] ABSTRACT

A method of characterizing pregnant female myometrial activity to distinguish between myometrial activity predictive of term or preterm labor and of contractures, which method comprises: (a) sensing discrete epochs of myometrial contractility and producing signals representing said discrete epochs; (b) storing said epoch representing signals; (c) determining characteristic repetitive frequencies of said signals and thereby determining whether the myometrial activity being characterized is predictive of term or preterm labor.

5 Claims, 5 Drawing Sheets

METHOD OF MONITORING LABOR

BACKGROUND OF THE INVENTION

As described in U.S. Pat. No. 4,500,523 and elsewhere, the myometrium contracts spontaneously throughout gestation. This activity has been confirmed experimentally in several species, including humans, by measuring increases in intrauterine pressure (IUP) (also sometimes referred to as intra-amniotic pressure (IAP) or changes in myometrial electromyographic activity (EMG). Continuous IAP and EMG recordings in chronically catheterized sheep show the presence throughout most of gestation of "contractures", EMG events of long duration (5–7 min.) that produce a small increase in IAP. The pattern of duration and frequency of activity events changes as labor approaches; Nathanielsz et al., Am. J. Obstet. Gynecol., 138:653 (1980); Krishnamurti et al., J. Reprod. Fert., 64:59 (1982).

It is further known through the study of electromyographic activity (EMG) in pregnant rhesus monkeys that at least two types myometrial activity occur during pregnancy. One of these, sometimes named Type I and associated with labor and delivery, is characterized by frequent bursts (e.g. 10 to 45 per hour) of electrical activity that last from 0.5 to 1.2 minutes. The other type of EMG activity observed, sometimes named Type II, and associated with spontaneous myometrial contractions during the normal development non-labor and delivery stages of pregnancy, consists of fragmented series of discharges that last 2 to 15 minutes and occur up to six times an hour. The frequency of Type I EMG events when present generally show a 24 hour pattern of low amplitude with a maximum at night. This daily pattern is amplified during the 8–10 days preceding delivery.

The pregnant rhesus monkey has been extensively investigated to study changes in myometrial activity and responses to various physiological and pharmacological agents. In this species myometrial electromyogram (EMG) electrodes and sensors for measuring intrauterine pressure (IUP) can be placed at the beginning of the last third of gestation or even earlier. Several groups of investigators have shown varying degrees of activity at different times of the 24 hour day during various stages of gestation [Harbert, Am. J. Obstet. Gynecol., 129:401–408 (1977); Harbert et al, Am. J. Obstet. Gynecol., 138:686–696 (1980); Taylor et al, Am. J. Obstet. Gynecol., 146:557–567 (1983); Ducsay et al, Am. J. Obstet. Gynecol., 145:389- (1983); Nathanielsz et al, In "Animal Models in Fetal Medicine" Vol. III Ed. Nathanielsz, Perinatology Press, Ithaca, New York pp 110–160 (1984)]. These cycles of myometrial activity have a clear temporal relationship to the circadian hormone changes in maternal and fetal plasma.

In pregnant sheep and monkeys, epochs of myometrial activity differing in duration and intensity have been described; Nathanielsz et al, In: "The Fetus and Birth" Ciba Foundation Symposium 47 Amsterdam, Elsevier pp 73–91 (1977); Nathanielsz et al, Am. J. Obstet. Gynecol., 138:653–659 (1980). One method of assessing the nature of activity at any moment is to characterize duration and amplitude of each individual event of myometrial EMG activity or IUP change either together or separately. In the sheep we have described computer based methods for the determination of duration of individual epochs of activity; Figueroa et al, Am. J. Obstet. Gynecol., 151:524–531 (1985). A preliminary description of similar event or epoch counting methods for use in the pregnant rhesus monkey has been presented to the Physiological Society, Cambridge, England, July 1984. In sheep, throughout the majority of gestation the most common epochs of myometrial activity are contractures, i.e. Type II activity, which we have defined as long duration epochs of increased IUP or EMG activity lasting more than three minutes [Jansen et al, Am. J. Obstet. Gynecol., 134:766–783 (1979); Nathanielsz et al, 1980, supra; Figueroa et al, 1985, supra; Harding et al, Am. J. Obstet. Gynecol., 142:448–457 (1982)]. At labor and delivery, myometrial activity shows a contraction type pattern during which the epochs of activity are shorter than two minutes, i.e. Type I activity. To obtain a clear impression of the type of myometrial activity under different physiological conditions, contractures need to be distinguished from labor and delivery contractions. Assessment of myometrial activity as Montevideo Units or area of activity under a pressure curve does not permit such a distinction since by using these methods one loses important information on duration and frequency of individual epochs of activity.

BRIEF DESCRIPTION OF THE DRAWINGS

FIG. 1 (B) is the myometrial EMG at the same time as (A), calibration bar 50 $\mu$V. The running mean threshold baseline (e.g. see Figueroa et al, supra) has been removed in both A & B; FIG. 1 (C) is the power spectral analysis of the IUP recording in A; FIG. 1 (D) is the power spectral analysis of the EMG recording in B.

FIG. 2 (B) is the myometrial EMG at the same time as (A), calibration bar 50 $\mu$V. The running mean threshold baseline has been removed in both A & B; FIG. 2 (C) is the power spectral analysis of the IUP recording in A; FIG. 2 (D) is the power spectral analysis of the EMG recording in B.

DESCRIPTION OF THE INVENTION

Figure 1:
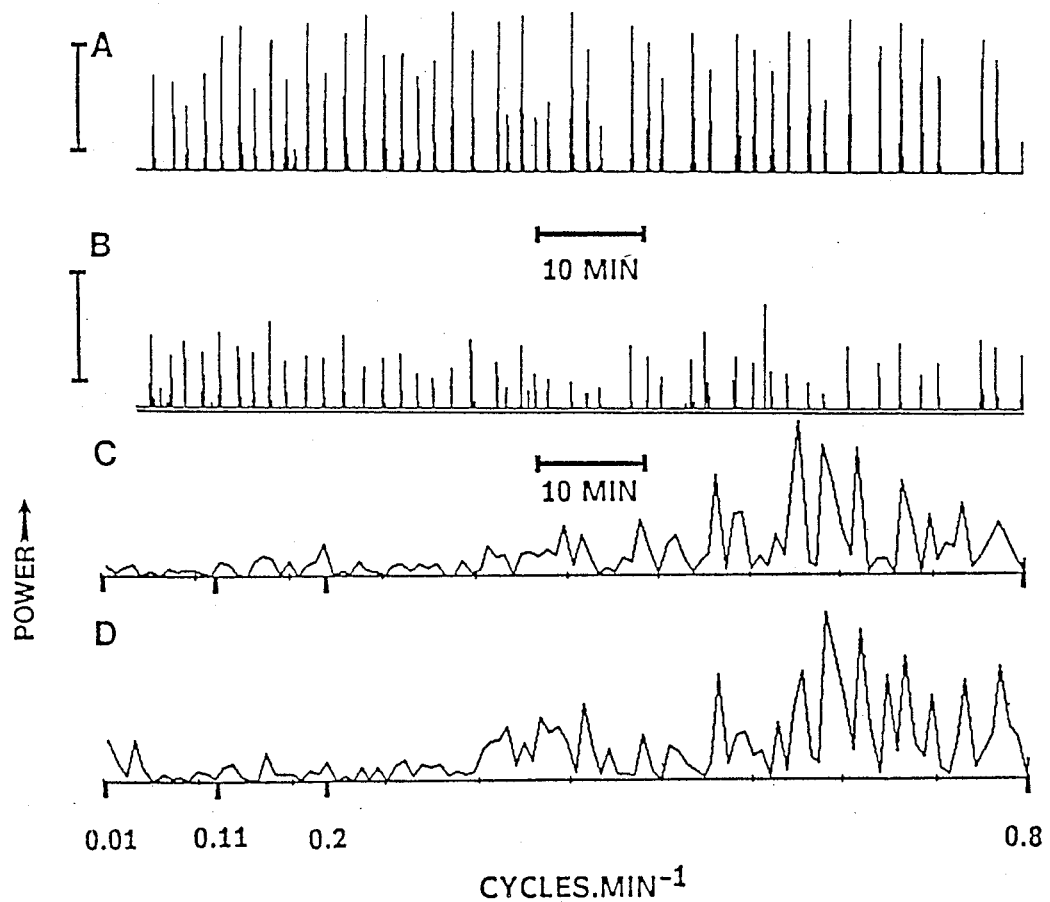
FIG. 1 (A) is the intrauterine pressure recording in a pregnant rhesus monkey one day post surgery, calibration bar 10 mm.Hg.

This invention relates to a method of characterizing pregnant female myometrial activity to distinguish between myometrial activity predictive of term or preterm labor (hereinafter sometimes referred to as Type I activity) as compared to innocuous contractures (hereinafter sometimes referred to as Type II activity). The method comprises sensing discrete epochs or individual events of myometrial contractility and producing signals representing these discrete epochs. The signals are stored and analyzed or processed to determine characteristic, repetitive frequencies of the signals, to thereby determine whether the myometrial activity being monitored is predictive or indicative of term or preterm labor.

The method of the invention allows the caregiver to more accurately determine at an early stage whether a given myometrial activity in a patient is innocuous or ominous, since the determination of the repetitive frequencies of the signals is a clearer, more rapid indication of whether particular activity is Type I activity or Type II activity, as compared to attempting the separation of the two types of signals on a visual or mathematical manipulation addressing the duration of epochs alone.

If desired, the characteristic repetitive frequencies of the signals, once determined, can be compared to a standard catalog of signals derived from prior documented cases, or alternatively, to a stored library of the patient's own previous signals to assist in the determination of whether a particular characteristic repetitive frequency is innocuous or ominous.

The sensing of myometrial contractility can be done in a number of ways using sensors known and available to those skilled in art. The sensors may be invasive or non-invasive. One can measure electrical impulses, pressure, heat, chemical changes (e.g. nuclear magnetic imagining of metabolic changes in the myometrium), or deformation of the uterine profile (in the latter case, for example, using ultrasonic measurement) caused by the myometrial contractility. The sensing means can generate a signal which can be analog or digital. In the presently preferred embodiment analog wave forms are converted to digital signals, since they are more readily manipulated by the presently preferred characterization techniques.

The resultant signals are stored, for example in a computer memory and analyzed or processed to determine the characteristic repetitive frequencies of the signals, the repetitive frequency being a characteristic of whether the sensed myometrial activity is Type I or Type II activity. Provided the analyzing or processing means generates the characteristic repetitive frequency value which is characteristic of Type I or Type II activity, the precise nature of the analyzing or processing method is not critical. The presently preferred method of signal processing involves Fast Fourier Transform and Power Spectrum Analysis. Other methods, for example, using Fourier Transform can also be used.

The FFT is a method of analyzing the waveforms of the signals produced by the sensors which respond to myometrial activity. Instead of separating the waveforms representing individual epochs of activity for analysis, the analysis of the present invention is made on the composite waveform produced by the sensors over a relatively long time period, encompassing a multiplicity of epochs of activity. The composite waveform is subjected to FFT analysis, to decompose the waveform into its characteristic, or repetitive, frequency components. The FFT analysis provides not only an indication of the characteristic repetitive frequencies which make up the composite waveform, but the amplitudes of those repetitive frequencies as well. These repetitive frequencies will correspond to the frequencies of the myometrial epochs of activity measured by the sensors.

The range, or spectrum, of frequencies produced by the FFT is then analyzed by a power spectrum analysis to determine the predominant frequency ranges in which the repetitive frequencies fall, and thus provide a clear indication of the nature of the myometrial activity that has been measured. The FFT provides an indication of repetitive frequencies, and thus of the rate of occurrence of myometrial epochs, rather than simply the total number of epochs over a period of time, and it is the repetitive frequencies that provide the fingerprint that allows accurate analysis of the underlying events.

It is the retention of amplitude characteristics and the division of all observed activity epochs into repetitive frequencies at different frequency ranges, that allows an improved description of patterns of myometrial activity than was possible with analysis based solely on counts of individual epochs of activity, or Montevideo Units, or computed area under the curve of the raw EMG or IUP signal as had previously been done. Dependent on the rate of sampling and the frequency of the waveform, FFT and power spectrum analysis can be performed over variable periods of time as appropriate to the activity under study. Thus, one can compare myometrial activity for many hours at different times of the day on successive days or for short periods following administration of various drugs.

It has been discovered that the analysis of the power spectrum of the sensed signals, for example IUP or EMG, readily distinguish between Type I and Type II activity. Frequencies below 0.2 cycles.min$^{-1}$ (i.e. less than one cycle every 5 minutes), preferably below about 0.15 and most preferably between about 0.01 and about 0.11 are indicative of Type II activity; while frequencies above 0.2 cycles.min$^{-1}$ or even higher, preferably between 0.2 to 0.8 cycles.min$^{-1}$ are indicative of Type I activity.

EXAMPLE

The purpose of the present study was to determine whether FFT and power spectrum analysis of uterine EMG and IUP make possible rapid distinction of different patterns of myometrial activity. In particular this study demonstrates that these methods permit clear distinction of contraction type activity that is characteristic of labor and delivery. FFT and power spectrum analysis of both myometrial EMG and IUP in the pregnant rhesus monkey obtained during three different situations were performed; immediately postsurgery, following food withdrawal and during treatment with the prostaglandin synthetase inhibitor indomethacin.

METHODS

Care of Animals

Surgical Procedures: Ten pregnant rhesus monkeys of known gestational age were obtained from the California Regional Primate Center, Davis CA and acclimated to the laboratory conditions as previously described., [see Nathanielsz et al in Animal Models in Fetal Medicine Vol. III Ed. Nathanielsz, Perinatorlogy Press. Ithaca, New York pp. 110-160 (1984); Binienda et al, Am. J. Obstet. Gynecol. 1988 (in press)]. The animals were housed in rooms with controlled light cycles, 14:10 hours light dark, with lights on at 08:00. Food provided was Purina 5045 Monkey Chow and fresh fruits. Water was provided ad libitum during the experimental period. At surgery monkeys ranged from 92.107 days gestational age (d G.A.). Animals were instrumented using techniques also described in the two aforementioned references. Briefly, under halothane anesthesia catheters were placed in the maternal femoral artery and vein in all ten animals. In each animal, two pairs of myometrial EMG leads were placed on the anterior wall of the uterus. In six animals, two catheters made of tygon microbore tubing (Norton Performance Plastics, Akron, Ohio) i.d. 1.27 mm, o.d. 2.29 mm, with a side hole one cm from the tip, were placed with 3 6 cm of the catheter within the amniotic cavity. A small retaining collar of tygon prefabricated around the catheter was located just within the uterus. Heparinized arterial blood samples were drawn at 10:00, 15:00 and 21:00 hours on most days for various hormonal analyses (not reported here). No experimental intervention was begun for at least five days after surgery.

Indomethacin protocol

In one animal, which was undergoing spontaneous contractions at 132 d G.A., indocin (Merck, Sharpe and Dohme) was administered via the maternal inferior vena caval catheter as an infusion of 6 mg.h$^{-1}$ starting at 15:30 and finishing at 21:00.

Food withdrawal protocol

On days that animals were fed, fresh food was provided at 08:00 and the monkey was allowed to feed ad lib. Three animals were used in the food withdrawal protocols. Food was returned at 15:00 p.m. and the next 24 hour period was called the first day of food withdrawal. Food was offered ad libitum after exactly 48 hours of food withdrawal. Only EMG was recorded in the food withdrawal protocol.

Data acquisition and storage

Figure 6:
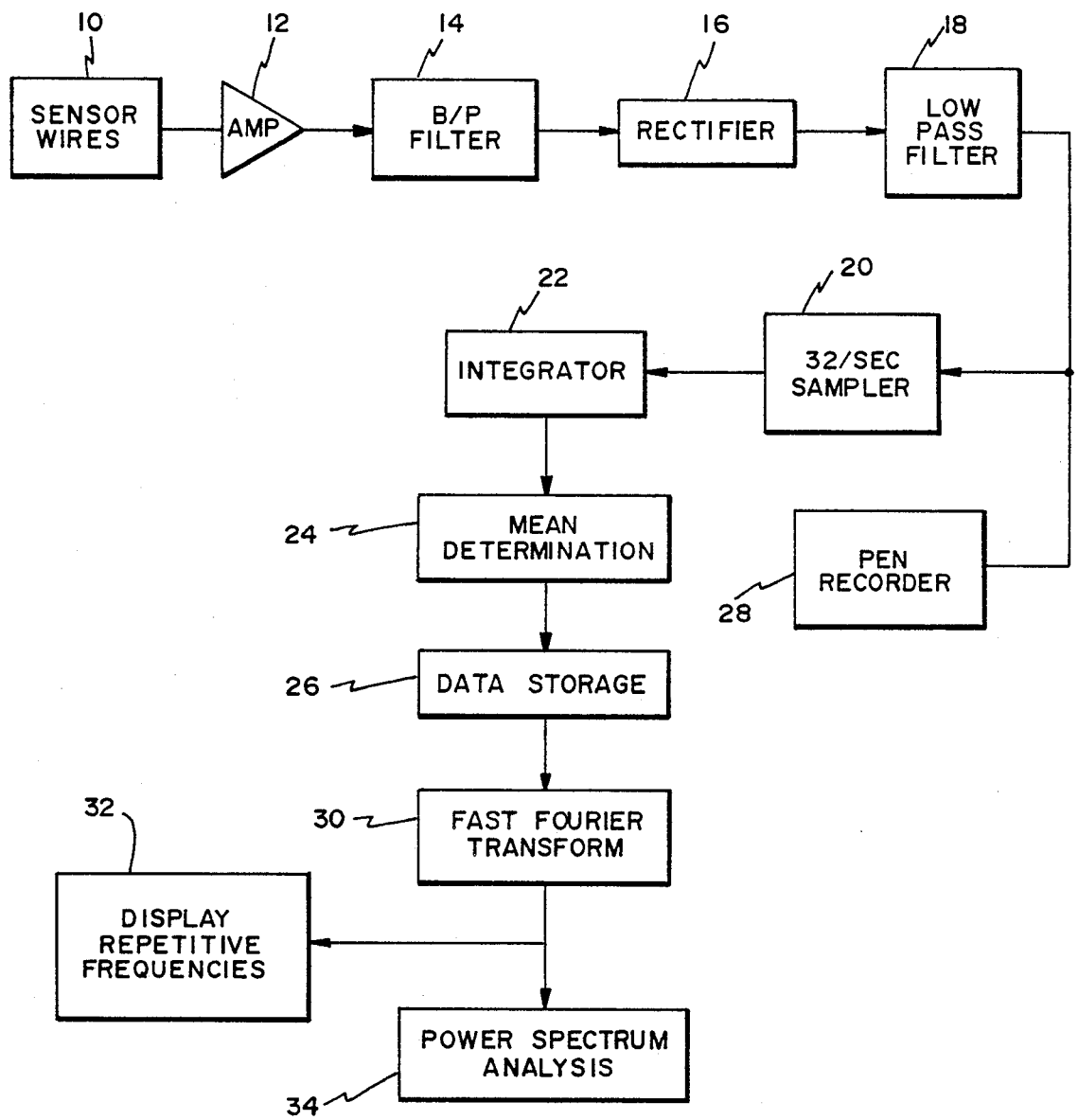
FIG. 6 is a schematic diagram of data acquisition and analysis in the Example

The uterine electromyogram was recorded from multistranded bipolar stainless steel wires (Cooner AS 632) implanted 3 to 5 mm apart in the mymetrium. The wires, illustrated in FIG. 6 at 10, were placed on at least two sites of the myometrium. As far as possible, the recording portion of the wire was sewn through all of the muscular layers of the uterus. The electromyographic signal was set for a 200 μV full scale deflection input amplified in amplifier 12, band-pass filtered in filter 14, (3 to 30 Hz), full-wave rectified in rectifier 16, and low-pass filtered (10 Hz) in fileter 18 to create the envelope of the electromyographic bursts. Each signal from filter 18 was sampled 32 times per second with 8 bit accuracy or 0.4% of full-scale deflection in sampler network 20 and the readings accumulated in integrator 22. At 8 second intervals, the mean activity for each channel of integrator 22 during that interval was computed at 24 from the accumulated values and transmitted, on a high-speed serial digital line, to an Apple II-based data collection and storage system 26 in a central monitoring room. The integrated uterine electromyographic activity is represented as units where one unit is 6.25 μV sec. The signals integrated over 8 seconds were stored on a floppy disk together with a time signal. To provide immediate display, the uterine electromyographic tracing was also recorded on a Beckman 711 pen-recorder 28. This record of activity was also used to verify the computer-based calculations. The initial sampling frequency of 32 Hz prevents aliasing problems with changing signals, while the lower storage rate of one reading every 8 seconds creates a manageable volume of data for subsequent analysis.

Data analysis

Fast Fourier Transform was performed as indicated at 30 on the digitized IUP and EMG data using Asyst 2.0 Software (Campbell et al, "Up and running with Asyst 2.0", MacMillan Software Co., 1987), and the results printed at display 32. Integration of the area under the curve for the Power Spectrum was performed at 32 by addition of all data points for the chosen range of cycle frequencies obtained from the FFT analysis.

STATISTICAL ANALYSIS

In the food withdrawal protocol, the integrated power spectrum data were analyzed by one way analysis of variance. The effect of the treatment was considered statistically significant when $p<0.05$. Data obtained during hours of daylight and hours of darkness were analyzed separately and not compared to each other.

RESULTS

Determination of power spectrum frequency windows that characterize contractions and contractures

In six animals the power spectrum of either IUP and/or EMG or both were analyzed for frequencies between 0.01 and 0.8 cycles per minute. Since there were no differences between power spectra of IUP or EMG data in the different frequency windows (FIGS. 1 and 2), data for percentage power indifferent windows of the IUP and EMG spectra were pooled for analysis of different patterns of contraction and contracture activity (Table I), to determine the percentage of total power at frequencies above and below three different cut offs - 0.11, 0.2 and 0.25 cycles per minute. Data were obtained from animals in the first five days post-surgery and were divided into periods when, by visual inspection, the activity was mostly contractions (Table IA) and when activity was mostly contractures (Table IB). Following evaluation of these data, quantification of contracture activity was performed on frequencies in the window 0.01 to 0.11 cycles.min$^{-1}$ (i.e. less than once cycle every 9 min) and contractions on frequencies in the window 0.2 to 0.8 cycles.min$^{-1}$ (i.e. greater than one cycle every 5 min).

TABLE I

Percentage of power spectrum activity above and below three different frequency levels in IUP and EMG records from six instrumented pregnant rehesus monkeys in the first five days post-surgery.

| | Cut Off - Cycles Per Minute | | | | | |
|---|---|---|---|---|---|---|
| | 0.11 | | 0.2 | | 0.25 | |
| | % Activity | | | | | |
| | Above | Below | Above | Below | Above | Below |
| A. CONTRACTIONS | | | | | | |
| MEAN | 95.4 | 4.6 | 83.6 | 16.4 | 71.8 | 28.2 |
| S.D. | 3.7 | 3.7 | 5.7 | 5.7 | 20.6 | 20.6 |
| B. CONTRACTURES | | | | | | |
| MEAN | 35.3 | 64.7 | 26.0 | 74.0 | 23.1 | 76.9 |
| S.D. | 13.9 | 13.9 | 10.9 | 10.9 | 10.0 | 10.0 |

Power spectral analysis of contractions

FIG. 1 shows the raw data trace for IUP and EMG at a time when only contractions are occurring. The good correspondence between IUP and EMG can readily be seen. For the EMG recording shown, 94.8% of the activity in repeating frequencies was at a greater rate than one every 5 minutes (a frequency $>0.2$ cycles.$min^{-1}$). For the IUP recording shown, 97.1% of the activity in repeating frequencies was at rates greater than one every 5 minutes.

Power spectral analysis of contractures

Figure 2:
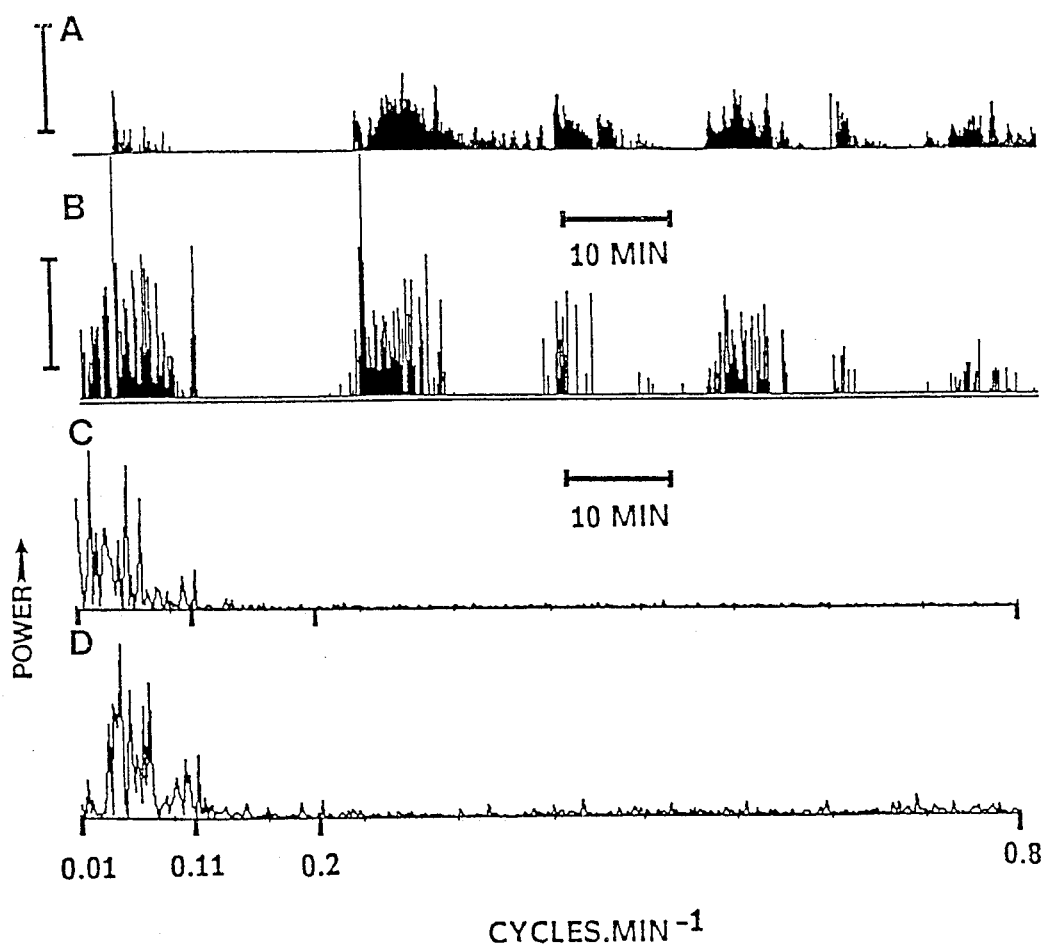
FIG. 2 (A) is the intrauterine pressure recording in a pregnant rhesus monkey three days post surgery. calibration bar 10 mm.Hg.

FIG. 2 shows the raw data trace for IUP and EMG at a time when only contractures are occurring. The good correspondence between IUP and EMG can readily be seen. For the EMG activity in the recording shown, 66.4% of the activity in repeating frequencies was at frequencies lower than one every 9 minutes (a frequency $<0.11$ cycles.$min^{-1}$). For the IUP in the recording shown, 83.5% of the activity in repeating frequencies was at rates slower than one every 9 minutes.

Indomethacin effect

Figure 3A:
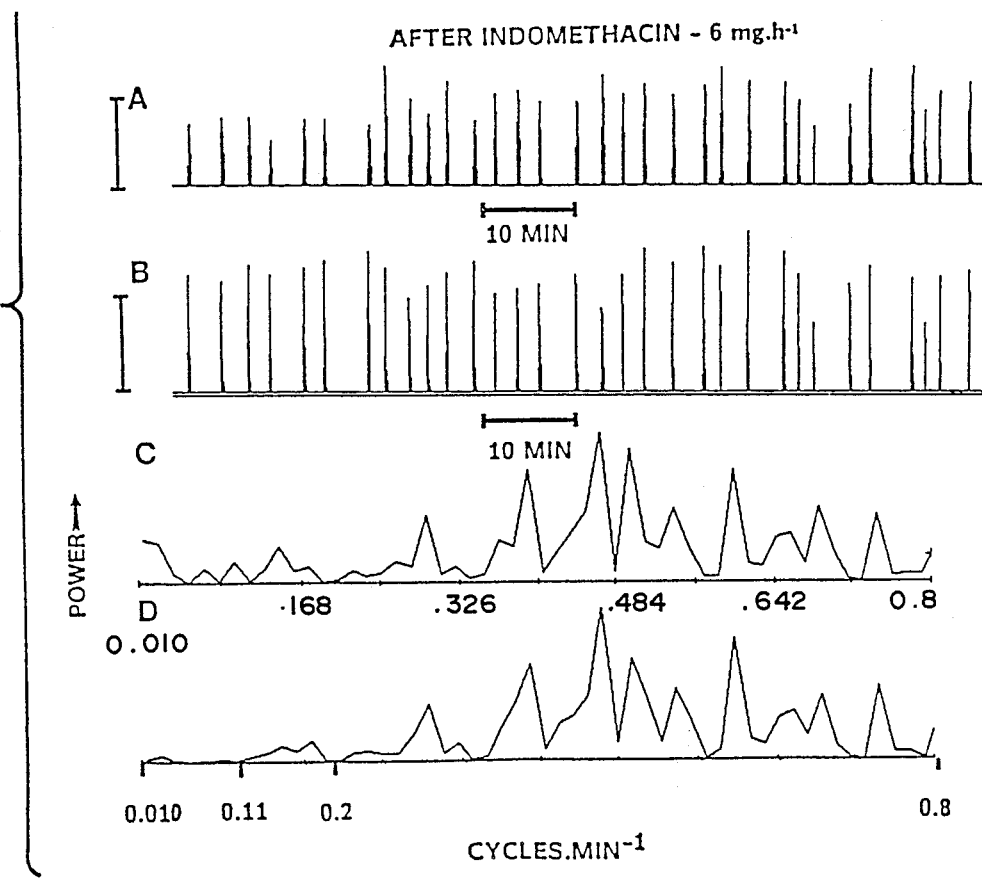
FIG. 3 is the myometrial electromyogram (EMG) and intrauterine pressure (IUP) in a pregnant rhesus monkey 132 days gestational age and 20 days postsurgery taken between 14:00 and 23:30 (a) before indomethacin; (b) during indomethacin infusion at 6 mg.h$^{-1}$ via the maternal aorta and (c) after cessation of indomethacin infusion. In each of FIG. 3a, 3b and 3c, (A) is the intrauterine pressure recording; calibration bar 10 mm.Hg; (B) is the myometrial EMG at the same time as (A), calibration bar 50 $\mu$V. The running mean threshold baseline has been removed in both A & B; (C) is the power spectral analysis of the IUP recording in A; and (D) is the power spectral analysis of the EMG recording in B.
Figure 3B:
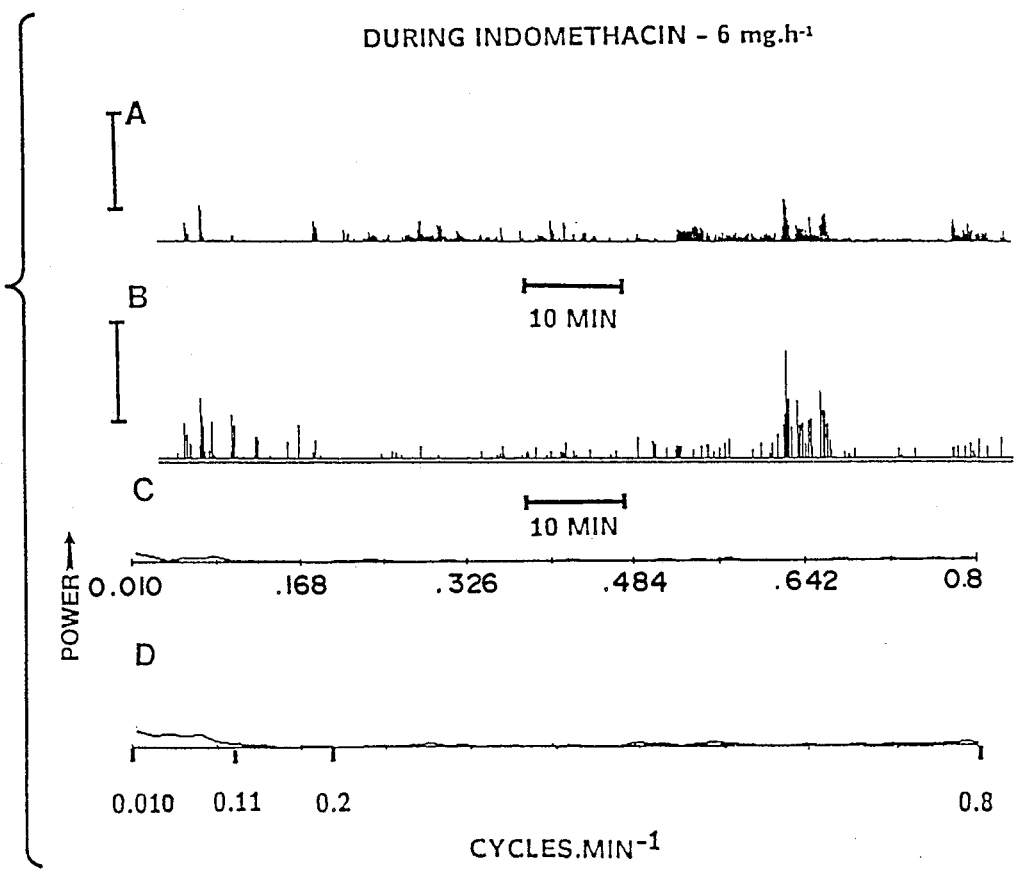
Figure 3C:
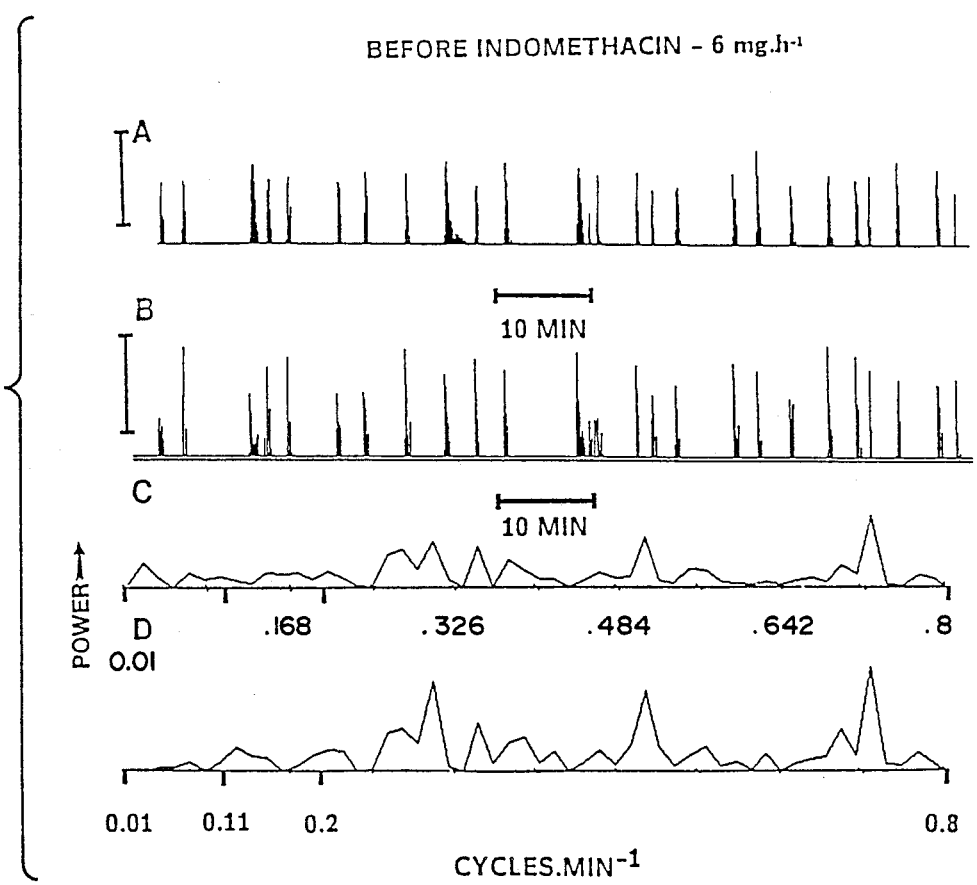

FIG. 3 shows the change in the power spectrum of IUP and myometrial EMG after a pregnant monkey that was having spontaneous contractions (FIG. 3(a)) was treated with indomethacin. During the period of indomethacin treatment, the majority of the power in the spectrum for both IUP and EMG has shifted to low frequency range (FIG. 3(b)) but after the contractions return, the power spectrum shifts back to high frequency range (FIG. 3(c)).

Food withdrawal

Figure 4:
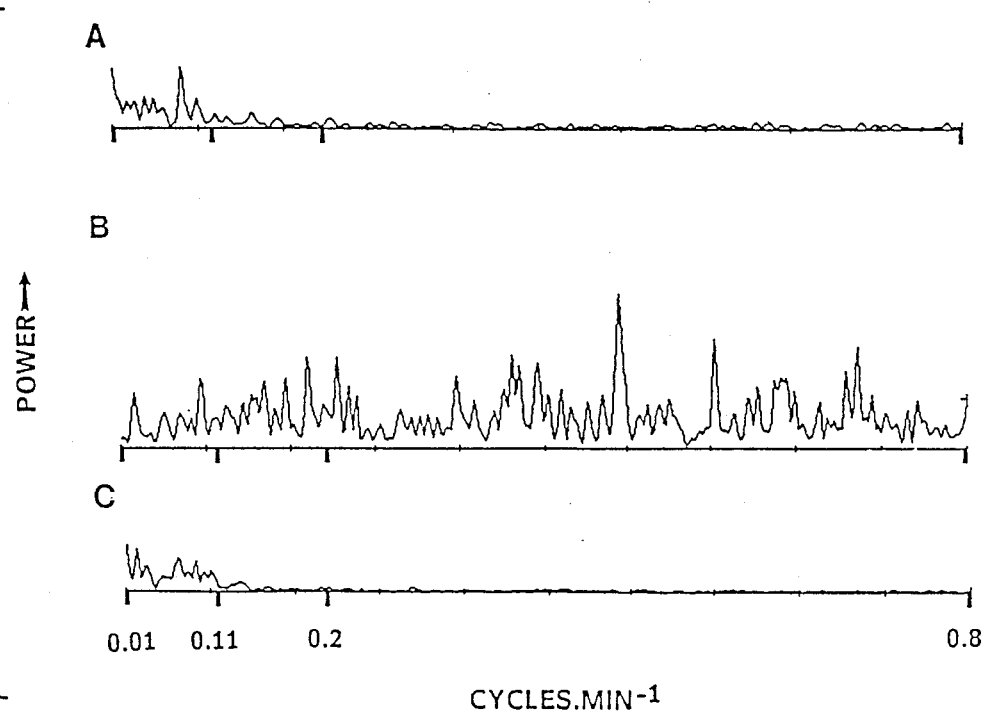
FIG. 4 shows data derived from the EMG recording from an instrumented pregnant rhesus monkey at 127 to 133 days gestational age and 28 to 34 days post surgery. Power spectrum of myometrial EMG between 20.00 (when lights go off) and 05:00 is presented at three times to show the effect of food withdrawal on the pattern of myometrial activity: A) the night before food withdrawal; (B) on the second night of food withdrawal and (C) the second night after food returned.
Figure 5:
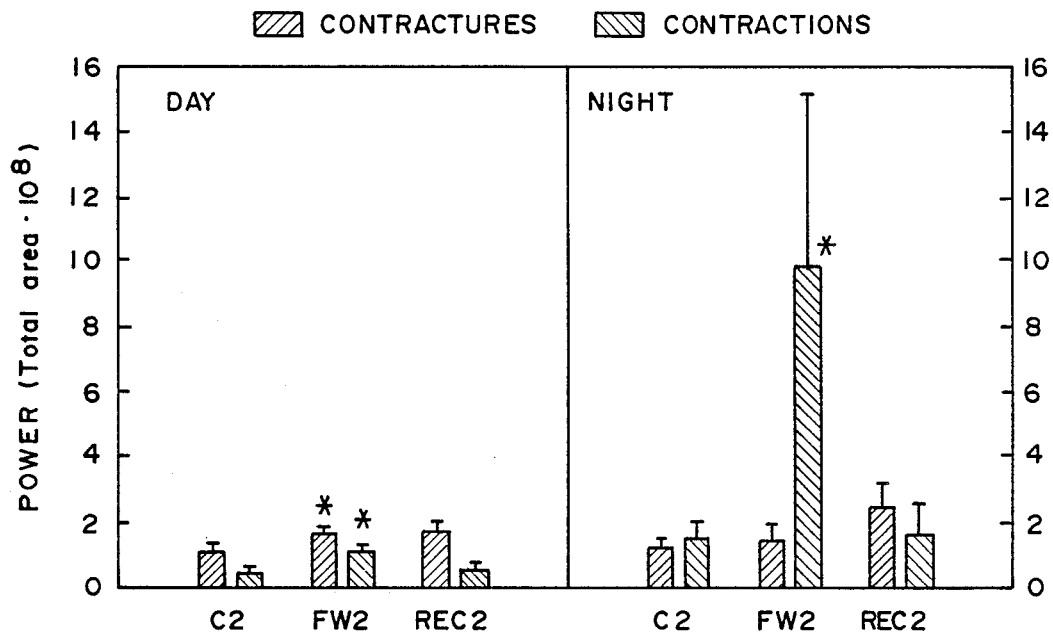
FIG. 5 is derived from the daylight (day) and darkness (night) power spectrum analysis data from three animals on the day and night before (control C2), the second night of (food withdrawal-FW.2) and second night after (REC2), food withdrawal (mean±S.D., n=3). Ordinate: total activity integrated under the power spectrum curve at frequencies greater than one every 5 min; total activity integrated under the power spectrum curve at frequencies less than one every 9 min. *A significant increase from $C_2$ ($p<0.05$).

The nighttime power spectrum for EMG in one animal the night before food withdrawal is shown in FIG. 4A. The majority of the spectral power is at frequencies less than one cycle every 9 min. On the second night of food withdrawal the power spectrum shifts to high frequency (FIG. 4B); after food is returned, the spectrum shifts back to low frequency (FIG. 4C). FIG. 5 shows the total power in the contracture and contractions portions of the nighttime power spectrum before, during and after the food withdrawal. By the second night of FW the activity in the contractions portion of the power spectrum had risen to 660% of the second control day ($p<0.05$). There was no change in the contractures spectrum. When the daytime power spectrum was analyzed control day 2, food withdrawal day 2 and recovery day 2 in the three animals from which food was withdrawn, the contractions portion of the power spectrum had risen to 270% of the second control day ($p<0.05$). The contractures portion of the power spectrum also increased significantly above that on control day 2 (FIG. 5).

DISCUSSION

FIGS. 1 and 2 demonstrate the excellent correspondence between the power spectra of IUP and EMG. It is sometimes impossible to obtain good IUP recordings from pregnant animals. Movement artifacts, e.g., crouching and straining at stool will produce artificial changes in IUP that can only be distinguished from myometrial activity if simultaneous EMG is recorded. In addition, in some experimental paradigms it is preferable not to incise the uterus. Thus, it is reassuring that, over several hours, recordings of EMG have good correspondence to the information obtained from IUP. Studies with the pregnant sheep show that individual EMG complexes may not be accompanied by changes in IUP since prior to labor EMG activity may not be propagated over the whole uterus and local contractility of the myometrium may not be reflected by intrauterine pressure changes. At different times of the day and under different physiological situations we have noticed that in the pregnant monkey there may also be differences in the amount of IUP change generated by individual EMG complexes of similar amplitude and duration but we have not made a detailed study of this relationship. This relationship will be affected by factors that affect activation-contraction coupling such as the density of gap junctions.

When contractures alone were present, the power spectrum showed the majority of activity at low frequency. The exact frequency peaks will depend both on the envelope of duration of the individual contracture and their frequency of occurrence. When the raw data showed mostly contractures, 65% of the power was at frequencies less than one cycle every 9 min. When contractions predominated, 84% of the power was at frequencies higher than one cycle every 5 min. For future analysis of waveforms from any sensors of myometrial activity there has, therefore, been chosen two windows, less than one cycle every 9 min to represent contracture activity and greater than one cycle every 5 min for contractions patterns.

Quantification of myometrial activity is important if assessment is to be made of changes throughout gestation and response to individual pharmacological agents. The power spectrum maybe precisely quantified by analyzing the power within any spectral frequency range. Thus, this methodology retains amplitude characteristics. A further importance of this technique is that it enables information from many hours of recording to be condensed into an easily visible and quantifiable format.

Power spectrum may be used to compare myometrial activity of the same animal between different periods of time, such as the hours of daylight and the hours of darkness. In addition, direct comparison of the period before, during and after administration of drugs can be made. Thus, when indomethacin was infused into the maternal aorta, contractions were converted to contractures so that the power spectrum shifted to the low frequency. This effect was reversed when the indomethacin infusion was stopped.

Power spectrum analysis can also be used to demonstrate if changes occur at the same time of the day but at different periods of gestation or over successive days of an experimental protocol. For example, in the food withdrawal studies, the switch from contractures to contractions occurred exclusively at nighttime. In order to study physiological and pathophysiological regulation of myometrial activity (e.g. preterm labor) it is suggested that computer based power spectral analysis of features of myometrial activity be applied to the critical times of the day at which contracture activity switches to contractions. Power spectral analysis is a powerful tool in determining specific patterns of myometrial activity and in assessing which patterns are innocuous and which are ominous.

What is claimed is:

1. A method of characterizing pregnant female myometrial activity to distinguish between myometrial activity predictive of term or preterm labor and of contractures, which method comprises:
    (a) sensing discrete epochs of myometrial contractility and producing signals representing said discrete epochs;
    (b) storing said epoch representing signals;
    (c) determining characteristic repetitive frequencies of said signals and thereby determining whether the myometrial activity being characterized is predictive of term or preterm labor.

2. A method as in claim 1 where the sensing senses at least one of intrauterine pressure or electromyographic activity.

3. A method as in claim 1 where the characteristic frequencies are determined using Fast Fourier Transform.

4. A method as in claim 3 where the characteristic sequences are determined using Power Spectrum Analysis in conjunction with Fast Fourier Transform.

5. A method as in claim 1 where the activity predictive of term or preterm labor is demonstrated at between about 0.2 and about 0.8 cycles.min$^{-1}$.

* * * * *